United States Patent
Barringer et al.

Patent Number: 5,536,942
Date of Patent: Jul. 16, 1996

[54] METHOD AND ARRANGEMENT FOR DETERMINING FIBRE PROPERTIES BY NEAR-INFRARED-SPECTROSCOPY

[75] Inventors: Niklas Barringer, Höganäs; Stig Norder, Säffle, both of Sweden

[73] Assignee: Procheck AB, Helsingborg, Sweden

[21] Appl. No.: 196,207

[22] PCT Filed: Sep. 11, 1992

[86] PCT No.: PCT/SE92/00626
§ 371 Date: Mar. 11, 1994
§ 102(e) Date: Mar. 11, 1994

[87] PCT Pub. No.: WO93/05384
PCT Pub. Date: Mar. 18, 1995

[30] Foreign Application Priority Data

Sep. 12, 1991 [SE] Sweden .................. 9102643

[51] Int. Cl.⁶ .......................................... G01N 21/35
[52] U.S. Cl. .................. 250/339.12; 250/334.07; 250/343
[58] Field of Search ............ 250/339.12, 339.07, 250/339.11, 341.1, 343; 162/49

[56] References Cited

U.S. PATENT DOCUMENTS

| | | |
|---|---|---|
| 4,743,339 | 5/1988 | Faix et al. . |
| 4,971,441 | 11/1990 | Damlin et al. .................. 356/338 |
| 5,104,485 | 4/1992 | Weger .................. 250/339.12 |

FOREIGN PATENT DOCUMENTS

| | | |
|---|---|---|
| 315737 | 5/1989 | European Pat. Off. . |
| 344694 | 12/1989 | European Pat. Off. . |
| 3504486 | 8/1986 | Germany . |
| 3639552 | 6/1988 | Germany . |
| 452513 | 11/1987 | Sweden . |
| 453016 | 1/1988 | Sweden . |
| 463118 | 10/1990 | Sweden . |
| 8602162 | 4/1986 | WIPO . |
| 8607458 | 12/1986 | WIPO . |

OTHER PUBLICATIONS

"Svensk Papperstiddning" No. 16—1985, pp. 14–16 and 19–23.

*Primary Examiner*—Davis L. Willis
*Assistant Examiner*—Richard Honig

[57] ABSTRACT

A method and an arrangement for determining properties of fibers in a supension of said fibers with the aid of spectroscopic measurements carried out in a wavelength range within the near infrared range (NIR), comprising introducing the fiber suspension into a measuring cell (20) which is provided with a filter (35) and an outlet (47) at one end thereof; concentrating the fiber suspension in the cell while simultaneously measuring the absorbency until a predetermined value is obtained at that wavelength at which the measurement is effected, or for the highest peak of the registered spectrum, at which point supply of the suspension is stopped, the outlet (47) from the cell is closed and a complete spectrum within the wavelength range is registered, whereafter the sought properties of the fibers are determined in a computer unit on the basis of earlier calibrations carried out on samples of known fiber properties. An arrangement for washing a fiber suspension-sample includes a cylinder having a piston, piston rod and a filter which is mounted close to the end of the cylinder opposite the piston rod, so as to divide the cylinder into a large piston-accommodating chamber and a small chamber, wherein delivery pipes leading to the cylinder and outlet pipes extending therefrom are connected to the small chamber and inlet pipes through which sample is delivered to the cylinder and outlet pipes for washed sample are connected to the large chamber.

20 Claims, 5 Drawing Sheets

METHOD AND ARRANGEMENT FOR DETERMINING FIBRE PROPERTIES BY NEAR-INFRARED-SPECTROSCOPY

The present invention relates to a method of determining properties of a fibre or pulp-suspension, such as pulp kappa numbers, for instance, with the aid of near-infra-red-spectroscopy. The invention also relates to an arrangement for determining these properties and also to an arrangement for treating the suspension.

The kappa number of pulp is measured repeatedly during a wood-pulping process in order to monitor delignification of the pulp. These measurements are carried out manually and are highly time-consuming—each measuring process takes about 40 minutes. This manual measuring process includes determining the dry solids content of the suspension, diluting or thinning the suspension with water to a given, very precise concentration, adding a solution of permanganate and sulphuric acid to the system, adding a potassium iodine solution precisely 10 minutes later so as to interrupt the reaction, and titrating released iodine with a thiosulfate solution.

STFI (Svenska Träforskningsinstitutet) have recently developed a method in which the kappa number is measured with the aid of UV-spectroscopy. This method employs the use of a transparent cuvette through which a washed and diluted fibre suspension is passed, wherein the reflected and transmitted UV-light is measured over a time period of one minute. The kappa number is then calculated on the basis of these measurements and also on the basis of the concentration of the suspension.

According to a similar method developed by BTG, a pulp sample is taken from the pulp line and the sample is screened, the fibres repeatedly washed and the sample is thinned or diluted to a consistency within the range of 0.20–0.40%, whereafter the sample is circulated in a circuit in which the suspension is measured; whereafter the process is repeated subsequent to further thinning the sample. The measuring process is effected with the aid of two sensors, one for UV-light and one for visible light, wherein the lignin content is determined with the UV-sensor and the pulp consistency and the properties are measured, or determined, with the visible light sensor.

The drawbacks of these systems is that the systems are not time and temperature stable. Aging of the lens system and detectors results in drifts in the system which can result in measuring errors. Deposits in the optical part of the system can also result in drifting or deviation of the system. Variations in ambient temperatures and of sample temperatures can also influence the system in several ways. For instance, wavelength shifts and changes in the optical properties of the system and in the response characteristic of the detector can occur when the temperature changes. In addition to these stability aspects, it is also necessary to take into account that the pulp may contain different types of wood which give different absorbency spectra. The measurement values become widely spread unless sample specific calibrations are made at close intervals in conjunction with sample assaying processes.

U.S. Pat. No. 4,743,339 describes a method of determining the kappa number and other characteristic properties of a pulp-suspension with the aid of FTIR-spectroscopy (FTIR =Fourier Transform InfraRed). According to this method, the infrared absorption is measured within the IR-range of the non-diluted sample in a transparent cuvette within the wave number range of 1600–1700 cm (the wavelength range of 6300–7800 nm). The kappa number can be determined subsequent to correcting the spectrum of the base line, whose level is determined by the water content and the fibre concentration of the sample. 200 sweeps within the wavelength range are required for each sample. The drawback with this method is that measurement accuracy is determined to a high degree on just how precisely the base line correction can be carried out. It is necessary to recalibrate the spectrometer for each type of pulp, process and sampling station in the station. Furthermore, it is necessary to carry out the measuring processes at room temperature.

The object of the present invention is to provide a method and an arrangement for assaying automatically a pulp-suspension or other fibre or particle suspensions of different fibre properties, such as to determine the kappa number, in which the drawbacks of the known methods are avoided and in which said suspension can be assayed swiftly without needing to calibrate for different types of process and wood. Neither shall the system be dependent on the concentration of the sample taken.

Accordingly, the present invention relates to a method of determining different properties of fibres in a fibre suspension with the aid of a spectroscopic assaying process carried out within a wavelength range within the near infrared range (NIR), comprising the steps of introducing the fibre suspension into a measuring cell which is provided with a filter and an outlet at one end thereof, concentrating the fibre suspension in the cell while simultaneously measuring the absorbency, either at a given wavelength or by sweeping the wavelength range, until a predetermined value is obtained at the wavelength at which the measuring process is conducted, or for the highest peak in the spectrum registered, whereat the supply of suspension is stopped, the outlet from the cell is closed and a complete spectrum within the wavelength range is registered, whereafter the concentrated sample is optionally returned to the suspension, therewith homogenizing the suspension and an additional quantity of liquid, whereafter the suspension concentrating and measuring processes are repeated, these steps optionally being repeated several times, and whereafter the fibre properties sought for are determined in a computer unit on the basis of earlier calibrations performed on samples having known fibre properties.

Calibrations made on one instrument shall be transferable to another instrument, which does not therefore need to be recalibrated.

The sample suspension is thus thickened until the absorbency value of the highest peak within the wavelength range, suitably 850–1050 nm in a pulp-suspension, reaches a given value. This absorbency maximum shall be independent of the property to be determined. In the case of a pulp-suspension, the highest peak, which is independent of the lignin content, is generally found at about 950 nm. The predetermined absorbency value may lie within the range of 2.0–4.5 absorbency units, e.g. 2.6 absorbency units. There is then registered or recorded a complete spectrum which consists, e.g., of about 100 measuring points, i.e. measurements are taken in steps of 2 nm. The concentrated sample is then optionally diluted and homogenized with a non-concentrated part of the sample suspension, whereafter the sample is reconcentrated and a complete spectrum is again registered. This process can be repeated several times, for instance from 1–8 times, preferably about 5 times.

Different properties of the fibres can be predicted from the spectra obtained, provided that calibration has been effected with mutually similar samples having known properties. The calibration work is exceedingly important so that the predictions obtained can be relied upon. For instance, when determining kappa numbers, it is necessary to cover the entire contemplated measuring range with measurements carried out on samples of known kappa numbers. This calibration process must also include samples that contain different types of wood. A calibration that has been carried out for a given instrument, however, can be transferred to a new instrument, thereby greatly increasing the usefulness of the method. During the calibration process, all measurement data is collected in a mathematical model and an evaluation is carried out with the aid of the so-called PLS-method (partial least square). Reference is made to H. Martens and T. Naes, "Multivariate Calibration", John Wiley & Sons Ltd., 1989, N.Y., for a more detailed description of the algorithms on which the calibration process is based. The contribution, i.e. the weight, of the kappa number is calculated for each wavelength. When the sample is analyzed, the kappa number is evaluated with the aid of the following relationship:

$$\text{Kappa Number} = B_0 + B_1 X_1 + B_2 X_2 + \ldots + B_{100} X_{100}$$

In the main, calibration involves determining all of the B-terms contained in the above relationship. The X-terms are the corrected absorbency values measured for the sample. The sample kappa number is predicted in this way. Other fibre properties than kappa numbers, e.g. fibre length and viscosity, can be predicted in a similar fashion.

The measured fibre suspension may be a washed suspension of fibres deriving from a wood pulping process. The properties measured are, for instance, the fibre kappa numbers, the fibre lengths or the viscosity value, which is a measure of the molecular size of the cellulose. According to the present invention, it is also possible to e.g. measure a suspension of wheat bran which is treated for the removal of phytic acid with the intention of determining the content of such acid. Similarly, the properties of other organic or inorganic fibres or particles can also be determined.

Prior to concentrating and measuring a sample, the sample is preferably circulated in a closed sample homogenizing circuit. The sample is also homogenized prior to each further sample concentrating and sample analyzing process.

The sample quantity used in the method will have, for instance, a dry substance content of 15–45 g, preferably about 30 g. The dry substance is introduced suspended in liquid, suitably water, at a concentration of, e.g., 3%. The amount of suspension used is suitably about 1 l.

Since the system in which the analyzing or assaying process is carried out may initially contain water in conduits in which the sample is homogenized, the sample is diluted to a dry substance content of about 0.5% for instance.

Prior to introducing the suspension into the cell, there is preferably registered a reference spectrum on conditioning water present in the cell.

Since the suspension concentration process is stopped when the sample has reached a given concentration, as shown by the absorbency value for a given wavelength, not all of the sample will be analyzed. The amount of sample introduced into the cell will normally correspond to a dry substance quantity of about 3 g. This sample quantity is returned to the remainder of the sample and the suspension is homogenized with a further small quantity of water prior to carrying out a further sample concentrating and analyzing process. A comparison between the registered spectra is carried out in the computer and any large deviations in any of these spectra, e.g. due to sample inhomogeneities, can be compensated for when calculating the properties sought. The standard deviation can also be determined.

The sample used in the analyzing process is, e.g., a washed pulp-suspension sample. This sample may suitably be obtained by introducing a pulp-suspension sample taken from a pulp-suspension preparing method into a cylinder having a piston and piston rod and a filter mounted close to the cylinder end that lies opposite to the piston rod, wherein the piston urges the sample against the filter so as to press out the liquid present through said filter, whereafter rinsing liquid is drawn into the filter by suction, when the piston is drawn to its opposite position in the cylinder, whereby the filter cake thus formed is suspended in the inflowing liquid, whereafter the piston is again moved towards the filter so that liquid present in the cylinder will flow out through the filter. This pulp-washing process is suitably repeated a number of times and the sample is then transferred to the concentrating cell, optionally after homogenizing the sample with further liquid.

The invention also relates to an arrangement for determining properties of fibres present in a fibre suspension, for instance a pulp-suspension, by registering a complete spectrum within the near-infrared-range of a concentrated part of said fibre suspension, said arrangement including a suspension sample inlet pipe, an NIR-measuring cell which is provided at one end with a filter and an outlet pipe and which is provided at the other end with an inlet pipe for the introduction of the suspension sample into said cell, and means for registering or recording a complete absorption spectrum within a given wavelength range, and a computer unit for processing the registered spectra and for determining the fibre properties sought for on the basis of earlier calibrations.

The arrangement suitable includes a closed circuit in which the sample is able to circulate prior to being concentrated, so as to homogenize the sample. This circuit may include a sample tank and a pump. The arrangement may also include a conduit for delivering flushing water to the cell outlet pipe and through the filter.

The apparatus will also suitably include outlet pipes which are connected to the closed circuit via valves, for withdrawing the pulp-suspension upon completion of the analyzing process. These outlet pipes may extend back to the pulp process or to a sample-saving tank. Since no foreign substances have been added to the suspension obtained, said suspension being merely thinned with water, the suspension can be cycled back to the process, thereby avoiding contamination of the environment.

For the purpose of flushing clean the cell, including filter and inlet and outlet conduits, the arrangement will suitably include an open circuit to which water is delivered. The analyzing apparatus will suitably include a pulp-suspension washing arrangement connected to the suspension-sample delivery pipe.

The invention also relates to an arrangement for washing a fibre-suspension sample, this arrangement including a cylinder which houses a piston and a piston rod and a filter which is mounted close to the end of the cylinder opposite the piston-rod end, such as to divide the cylinder into a large piston-accommodating chamber and a small chamber, wherein the flushing-liquid delivery pipe and outlet pipes are connected to the small chamber and the inlet pipe through which sample is introduced into the cylinder and the outlet pipe through which washed sample is removed are connected to the large chamber.

The arrangement suitably includes a flushing-liquid outlet pipe which is coupled to the outlet pipe for washed sample.

The arrangement will preferably include a valve for each of the pipes leading to or from the cylinder. These valves are suitably controlled by a computer unit.

The arrangement is connected suitably to a cell in which the washed sample is concentrated and in which sample properties are determined spectroscopically.

The sample concentrating process includes a standardization which enables measurements to be taken on samples of varying concentrations and of different natures. Furthermore, the need to calibrate the system is reduced. When practicing the inventive method, it is not necessary to screen the pulp or fibre suspension, as distinct to known methods.

The invention will now be described in more detail with reference to a number of exemplifying embodiments thereof and also with reference to the accompanying drawings, in which FIG. 1 is a schematic view of an inventive analyzer;

Figure 1:
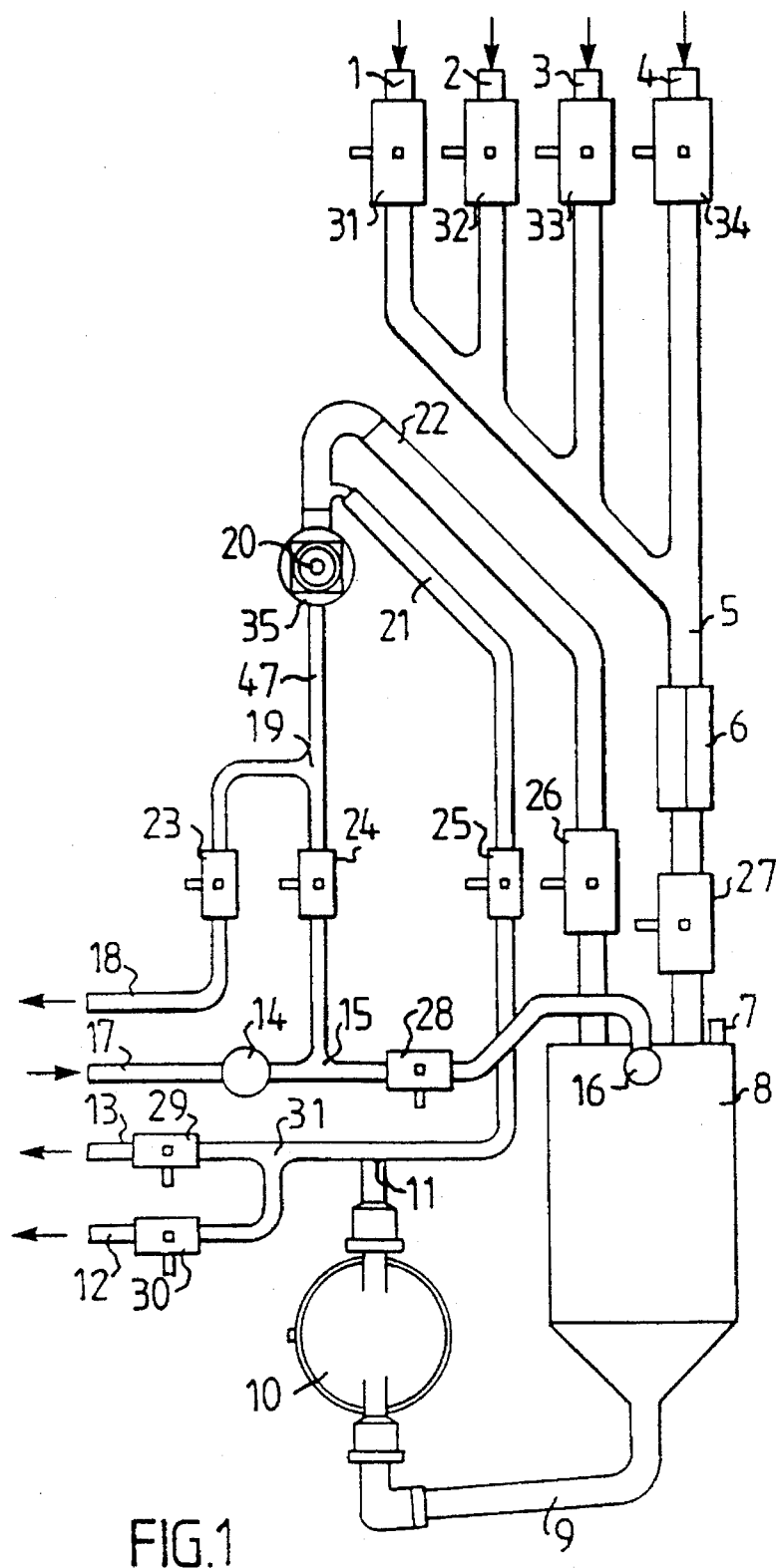

The arrangement illustrated in FIG. 1 is an arrangement suitable for carrying out the analysis method according to the present invention. This arrangement includes inlets 1–4 for samples taken from four different measuring points in a process. These samples are combined in an inlet pipe 5 which extends through a photoelectric switch 6 and a level sensor 7 into a sample tank 8. An outlet pipe 9 extends from the sample tank to a branch or junction point 11, via a pump 10, from which a pipe leads to a branch point 31, from which two outlet pipes 12, 13 extend, one of said outlet pipes being intended to conduct sample that is to be saved and the other being intended to conduct sample back to the process, each of said pipes being provided with a respective valve 30, 29. From the branch point 11 there also leads a pipe 21 which is provided with a valve 25 and which delivers sample to a measuring cell 20. A recycle pipe 22 having a valve 26 extends from the measuring cell 20 back to the sample tank 8. The measuring cell 20 includes a filter 35 and an outlet pipe 47 extends from the filter, from the cell, to a branch point 19 which leads to a valve 23 and a flushing-liquid outlet pipe 18 and also to a valve 24 and a further branch point 15 which connects a flushing-liquid inlet pipe 17 provided with a pressure monitor 14 to a pipe which extends to a spray nozzle in the sample tank 8, via a valve 28. The inlet pipes 1–4 are also fitted with valves 31–34.

The invention will now be described in more detail with reference to an exemplifying embodiment thereof and also with reference to FIG. 1. Sample can be taken from any desired number of measuring points, although the illustrated embodiment has been restricted to four measuring points. The sample shall consist of washed pulp. A total of one liter of sample is used. The paper pulp solution will preferably be about 3%, i.e. the dry substance content of the sample will preferably be 30 g or at least lie within the range of 15–45 g.

Prior to sampling and analyzing the system shown in FIG. 1 is conditioned with water or some corresponding flushing/rinsing solution. The sample tank 8 has a volumetric capacity of 12 l and although flushed out is not fully evacuated. The measuring cell 20 is also cleansed and filled with water. In the case of this example, sampling is effected via inlet 1. The following units are computer controlled: photoelectric switch 6, pump 10 and all valves 23–30, 32–34. The level sensor 7 and the pressure monitor 14 are also connected to the computer. The system contains from the start about 5–6 l water.

Step 1: Sample intake, washed sample.

The valves 31, 27 and 29 are opened. The pump 10 is started. The sample tank 8 is evacuated via the branch points 11 and 31 and out through the outlet pipe 13, at the same time as sample is advanced through the inlet pipe 5 to the photoelectric switch 6. The sample is registered by the switch and the pump is stopped when all the sample, about 1 liter, has been delivered to the sample tank 8, after which all valves are closed.

Step 2: Registering a reference spectrum.

A reference spectrum within the range of 850–1050 nm is registered for the water that is found in the measuring cell 20. This takes about 2 seconds and the number of measuring points selected is 100, i.e. a reading is taken at each alternate nanometer.

Step 3: Homogenizing the sample.

The valves 25 and 26 are opened. The pump 10 is started and homogenization effected by pumping the sample around the system, from the tank 8 through the pipes 9, 21 and 22 and back to the tank, thereby the sample is united with the water present in the system. This is continued for a period of about 4 seconds. The pump capacity is preferably about 120 l/min.

Step 4: Sample concentration.

The valve 26 is closed and the valve 23 opened. The pump 10 is still operating. The sample can now be concentrated in the measuring cell 20 in whose lower part a filter 35 is mounted, by pumping the sample from the sample tank 8 through the pipes 9 and 21 and into the measuring cell 20, where the sample is concentrated against the filter 35 while the surrounding liquid will continue to flow out of the measuring cell, to a slush recipient, via branch point 19, valve 23 and outlet pipe 18. The time taken to effect the sample concentrating cycle will depend on the properties and concentration of the pulp, but in general takes from 5–10 seconds to complete. During this pulp concentrating cycle, the sample is measured spectroscopically in the measuring cell 20, either continuously at a given wavelength in the range of 850–1050 nm, or by repetitive scanning within this range. The wavelength at which the absorbency is measured is chosen so that variations in sample composition will not appreciably influence the readings ("unbiased readings"). When a predetermined absorbency value in the range of 2.0–4.5 absorbency units (A.U.) is reached, the pump 10 is stopped and all valves are closed.

Step 5: Measuring spectrum registration.

The measuring process is now effected on a concentrated, stationary sample in the measuring cell 20, by registering a spectrum in the wavelength range of 850–1050 nm. As beforehand, a complete spectrum is comprised of 100 different measuring points.

Step 6: Rinsing or flushing the measuring cell.

The valves 24 and 26 are opened and the concentrated sample plug is then flushed away with water or some other suitable flushing liquid which is delivered to the system through the pipe 17, valve 24, branch point 19, measuring cell 20, pipe 22, valve 26, and down into the sample tank 8. This procedure returns the sample to its original state, although the sample is slightly more diluted than earlier.

Step 7: Repeated measuring cycle.

The same sample can now be measured once more by repeating the concentrating step (Step 4) and measuring step (Step 5). Further measurements, or analyses, can then be made by repeating the sequence of Step 6-Step 4-Step 5 a desired number of times. Five different measuring processes are normally carried out in this way on each sample.

Step 8: Sample evacuation.

The sample can now either be passed back to the process or saved for analyzing with alternative methods or for other purposes.

a) The sample is to be returned to the process. The valve 29 is opened and the pump 10 started-up. The sample is pumped to a slush recipient through the outlet pipe 9, the pump 10, the branch point 11, the branch point 31, the valve 29 and the outlet pipe 13. Rinsing or flushing liquid is then flushed through the inlet pipe 17 and into the sample tank 8, via valve 28 and spray nozzle 16. The pump 10 is stopped.

b) The sample shall be saved. The valve 30 is opened and the pump 10 started-up. The sample is pumped to a sample-collecting vessel, through the outlet pipe 9, the pump 10, the branch point 11, the branch point 31, the valve 30 and the outlet pipe 12. Rinsing or flushing liquid is then flushed through the inlet pipe 17 and into the sample tank 8, via the valve 28 and the spray nozzle 16. The pump 10 is stopped.

Step 9: Resetting the system.

The pump 10 is stopped and all valves are closed. The valves 24, 25 and 29 or 30 are opened, whereby self-pressurized rinsing liquid rinses out the measuring cell 20 and the pipe 21 and pipe 13 or 12. All valves are then again closed, such as to set the system in a waiting mode.

The time taken for a complete sample measuring cycle is about 2–4 minutes. The total amount of water consumed with each sample is about 10 l.

Figure 2:
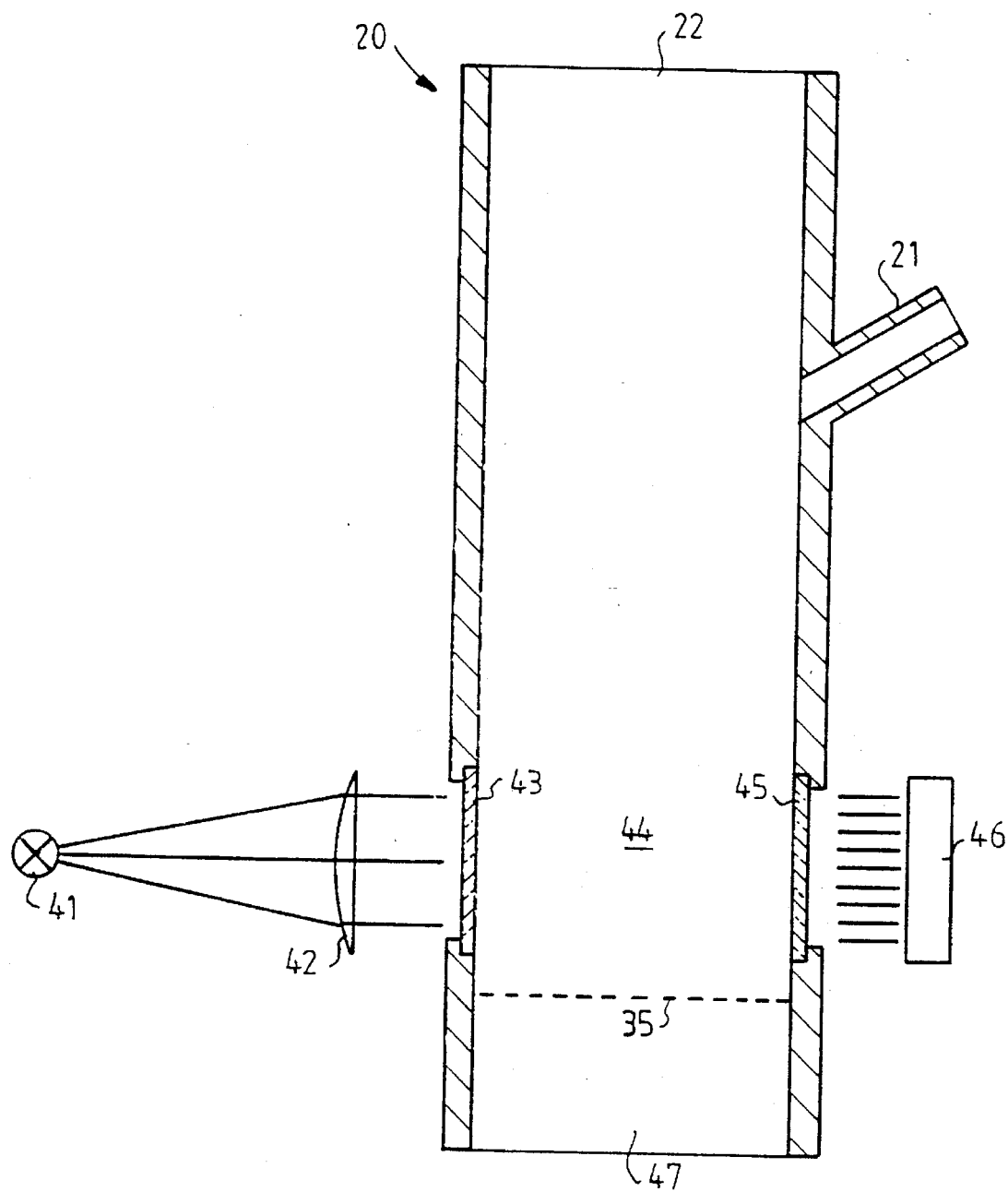
FIG. 2 is a view of the sample concentrating and measuring cell included in the analyzer shown in FIG. 1.

The construction of the measuring cell is illustrated in FIG. 2. Light from the light source 41 is collected by the lens 42 and is led in through a window 43 and through the centre 44 of the measuring cell. The non-absorbed light continues through the window 45 to the detector 46. The pulp suspension is led in through the delivery pipe 21 and is concentrated against the filter 35. When the measuring cell is evacuated, the sample leaves the cell through the outlet 22, which is effected by pumping flushing or rinsing liquid up against the filter 35, through the pipe 47.

Figure 3:
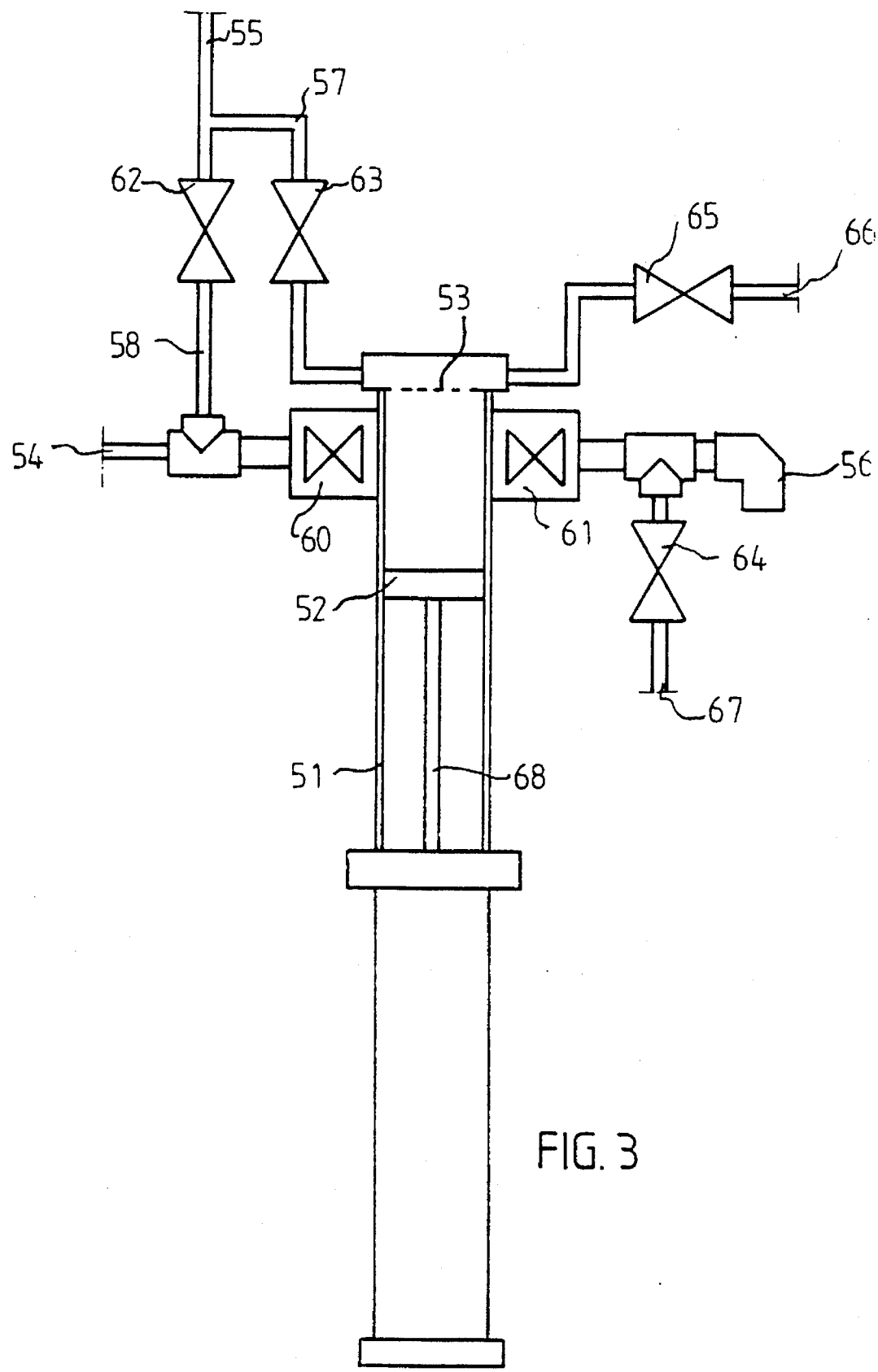
FIG. 3 illustrates schematically an inventive arrangement for washing fibre or pulp-suspensions.

The arrangement for flushing away a fibre or pulp sample is shown in FIG. 3. This arrangement includes a sample inlet pipe 54 which leads to a sample cylinder 51, via a valve 60. The sample cylinder 51 includes a piston 52, a piston rod 68 and a filter 53 which is mounted at the end of the cylinder 51 remote from the piston rod. A water or flushing-liquid inlet pipe 55 leads to a flushing-water pipe 57 which, in turn, leads to the cylinder at a point adjacent the filter 53, via a valve 63. A flushing-water outlet pipe 66 provided with a valve 65 extends from the same part of the cylinder. The inlet pipe 55 also extends to a flushing-water pipe 58 provided with a valve 62 and being connected to the sample inlet pipe 54. The washed sample is removed through a pipe 56, via a valve 61, to which a flushing-solution outlet pipe 67 is also connected, via a valve 64.

The principle on which the flushing or rinsing method is based will now be described. At the commencement of a sampling cycle, the piston 52 is located at its end position in the cylinder 51, so that the piston 52 will rest against the filter 53. All of the valves 60–65 are closed. These valves are controlled by a computer (not shown). Sample is drawn-in through the sample intake 54, by opening the valve 60 and moving the piston 52 downwards. About one-third of the cylinder 51 is filled with sample. Valve 60 is closed and valve 62 opened. Water will then flush the sample intake 54 clean of sample. Valve 62 is closed and valve 63 opened. The piston 52 is moved down to its lowest position, whereby water is drawn into the cylinder 51 and mixed with the sample. Valve 63 is closed and valve 65 opened. The piston 52 is now moved up into full engagement with the filter 53. The pulp is concentrated against the filter 53 and the flushing solution is removed to a slush recipient, via valve 65 and discharge pipe 66. Valve 65 is closed and valve 63 opened. The piston 52 is again moved down to its end position, whereafter valve 63 is closed and valve 65 opened. The piston 52 is moved up against the filter 53 and by repeating this flushing cycle, e.g. six times, there is finally obtained a washed sample which is ready for introduction into the analyzer. This is achieved by closing all valves with the piston 52 located in its lower end position, whereafter valve 61 is opened. The piston is moved upwards and the washed and diluted sample is pressed out through the pipe 56. The pipe 56 can then be flushed with the aid of the water flow taken in through the pipe 57, so that the remaining sample quantity is also recovered. In this regard, the valve 63 is opened for the time required to effect this flushing process. The sampling device is washed by taking in water through the pipe 57, the piston is moved down to its end position, the valves 61 and 64 are opened, the piston is moved up against the filter and the washing liquid is flushed out through the pipe 67. The method is repeated until the cylinder is absolutely clean.

A total amount of about 10 liters of water is used in the washing process.

Figure 4:
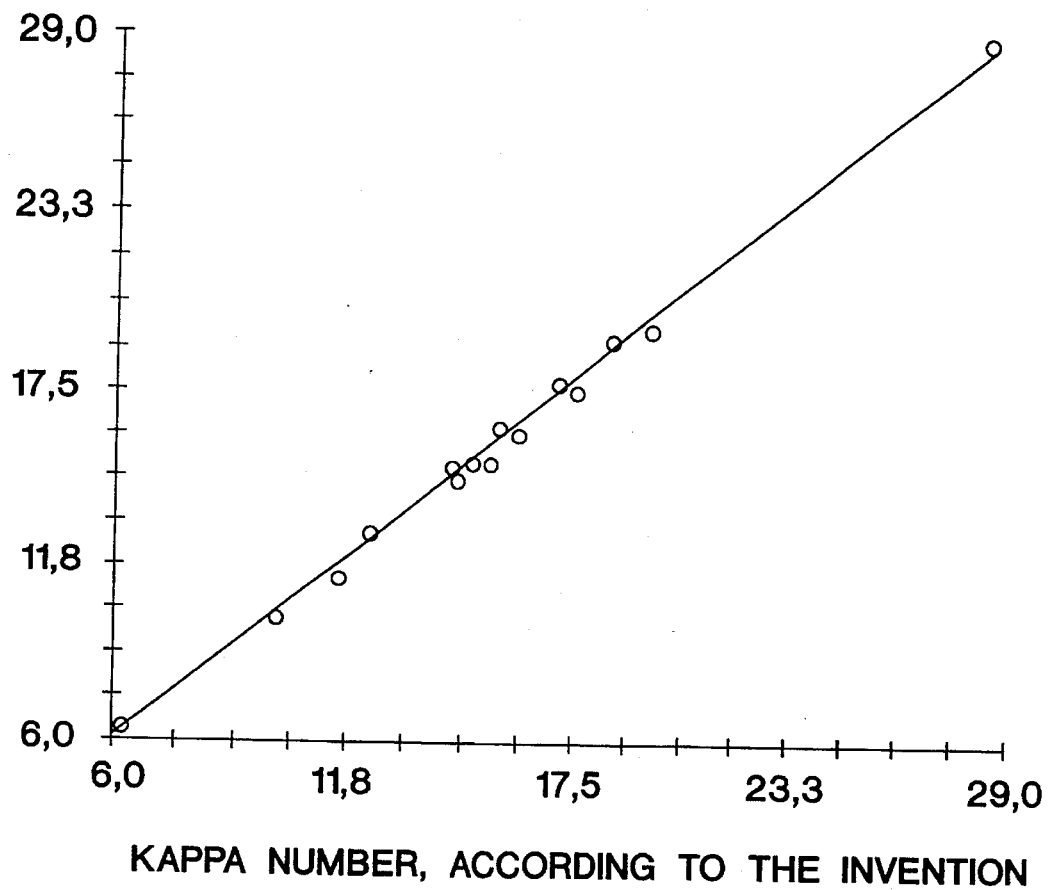
FIGS. 4 and 5 are diagrams showing the agreement between measuring processes carried out with the present arrangements and those carried out with conventional methods.

FIG. 4 illustrates kappa number determinations which have been made partly manually in accordance with current standard methods and partly in accordance with the present invention. A very good correlation is obtained.

Figure 5:
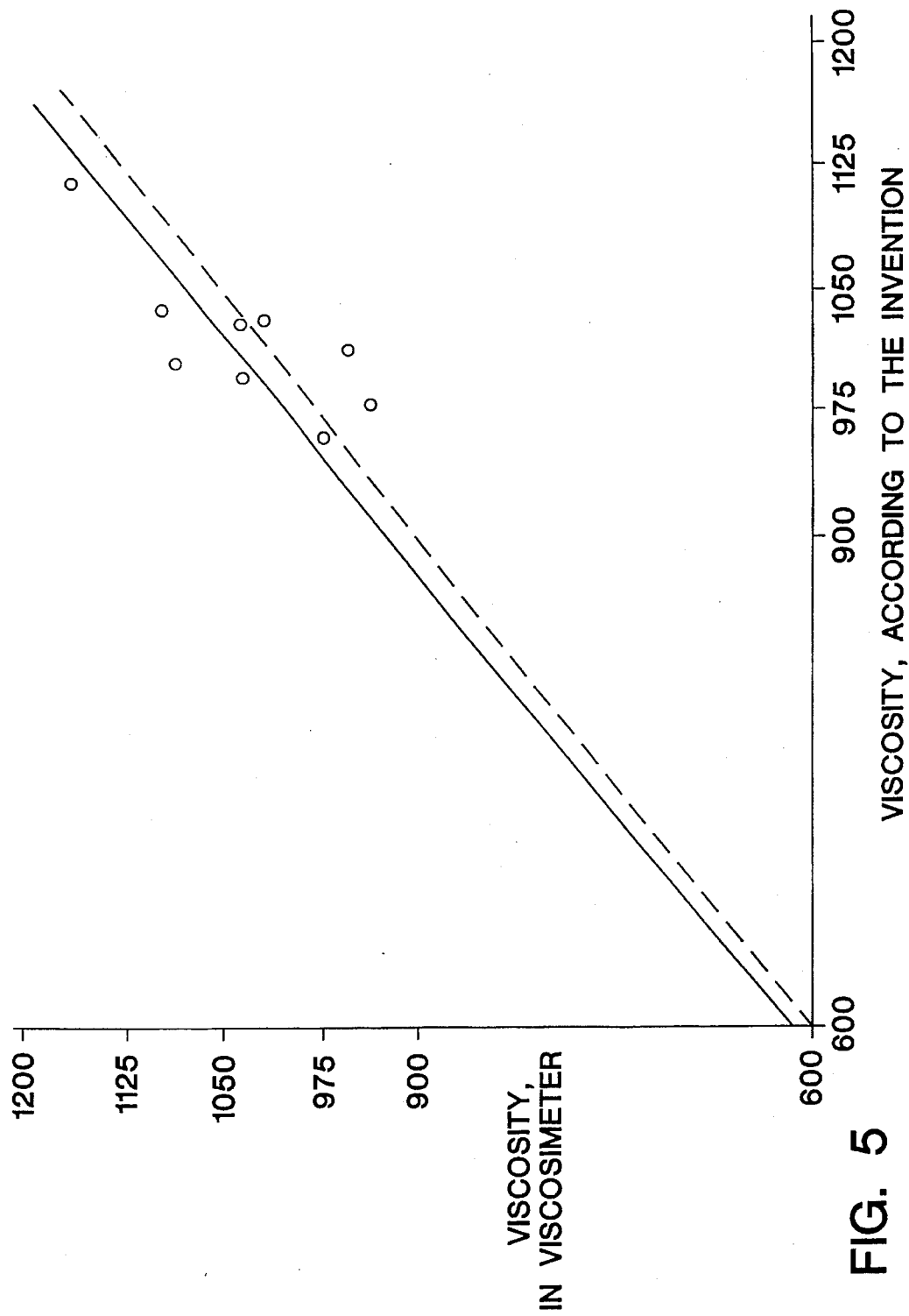

FIG. 5 illustrates viscosity determinations made partly manually by dissolving dried, homogenized fibre samples in water and copper ethylenediamine and partly in accordance with the present invention. Despite the fact that relatively few measuring points were used in the process of calibration, there is found a correlation which clearly indicates the potential of the invention.

Thus, it is possible when practicing the invention to determine very precisely different fibre and particle properties on particles and fibres in suspension. These measurements are not dependent on properties of the liquid suspension medium or on other fibre or particle properties. The inventive analyzing arrangement can be calibrated in a manner which will enable its calibrations to be transferred to other arrangements, therewith obviating the need for the user of the instrument to make separate recalibrations. The inventive method is also very rapid and does not result in contamination of the environment, since the sample taken can be returned to the process investigated.

We claim:

1. A method for determining properties of fibres in a suspension of said fibres with the aid of spectroscopic measurements carried out in a wavelength range within the near infrared range (NIR), comprising the steps of:

circulating a fibre suspension in a closed circuit to homogenize the fibre suspension;

introducing the fibre suspension into a measuring cell which is provided with a filter and an outlet at one end thereof;

concentrating the fibre suspension in the measuring cell while simultaneously measuring the absorbency, either at a given wavelength or by scanning the wavelength range, until a predetermined value is obtained at that wavelength at which the measurement is effected, or for a highest peak of a registered spectrum, at which point supply of the suspension is stopped, the outlet from the cell is closed and a complete spectrum within the wavelength range is registered, whereafter the concentrated sample is optionally returned to the suspension, which is homogenized with said sample and a further quantity of liquid, whereafter the sample concentrating and measuring process is repeated, these steps optionally being repeated several times, and whereafter the sought properties of the fibres are determined in a computer unit on the basis of earlier calibrations carried out on samples having known fibre properties.

2. A method according to claim 1, characterized in that the fibre suspension is a washed suspension of fibres that derive from a pulp process.

3. A method according to claim 2, characterized by determining the kappa number of the fibres.

4. A method according to claim 1, characterized by determining the lengths of the fibres.

5. A method according to claim 1, characterized by determining the viscosity of the suspension.

6. A method according to claim 1, characterized by concentrating the sample and measuring said sample from 1 to 8 times, particularly from 3 to 7 times, preferably 5 times.

7. A method according to claim 1, characterized by carrying out the measuring process over a wavelength range of 850–1050 nm.

8. A method according claim 1, characterized by allowing the sample to circulate in a closed circuit so as to homogenize the sample prior to concentrating and measuring the sample and prior to each optional additional sample concentrating and measuring process.

9. A method according to claim 1, characterized by delivering 14–45 g, preferably about 30 g of sample suspension to the sample analyzing or measuring unit, these quantities being based on the dry solids content of the suspension.

10. A method according to claim 1, characterized by registering a reference spectrum on the conditioning water present in the cell, prior to introducing the suspension into said cell.

11. A method according to claim 2, characterized by sweeping, or scanning, the whole of the wavelength range during the sample concentrating process and stopping concentration of the sample when the highest peak within this range exhibits a given absorbency value within the range of 2.0–4.5 absorbency units.

12. A method according to claim 2, characterized by measuring the absorbency at a given wavelength, preferably at about 950 nm, during the sample concentrating process, and stopping the sample concentrating process when a predetermined absorbency value is obtained within the range of 2.0–4.5 absorbency units.

13. A method according to claim 8, characterized by homogenizing the sample with liquid present in the closed circuit, prior to introducing the sample.

14. A method according to claim 1, characterized by introducing a pulp-suspension sample taken from a pulp manufacturing process into a cylinder provided with a piston and a filter close to one end thereof; causing the piston to press the sample against the filter so that liquid present in the sample will be pressed through the filter; withdrawing the piston to an opposite position in the cylinder so as to draw flushing liquid through the filter, whereby the resultant filter cake is suspended in the inflowing liquid; returning the piston towards the filter so that liquid present in the cylinder will flow out through the filter; repeating this pulp-washing process a number of times; and transferring the sample to the measuring device by closing valves externally of the filter so that the suspension present in the cylinder will exit therefrom through an outlet pipe.

15. An arrangement for determining properties of fibres present in a fibre suspension by registering a complete spectrum within the near-infrared-range (NIR) of a concentrated part of the fibre suspension, characterized in that the arrangement includes a suspension-sample delivery pipe, a measuring cell for NIR-measuring processes, said cell being provided at one end with a filter and an outlet pipe and at the other end with a suspension-sample inlet pipe, a closed circuit in which the suspension circulates to homogenize the suspension prior to the suspension sample concentration process and means for registering a complete absorption spectrum within a given wavelength range, and a computer unit for processing registered spectra and for determining the fibre properties sought on the basis of earlier calibrations.

16. An arrangement according to claim 15, characterized in that the closed circuit includes a sample tank and a pump.

17. An arrangement according to claim 15, characterized in that the arrangement includes a conduit for delivering flushing water to the measuring outlet pipe of the cell and through the filter.

18. An arrangement according to claim 15, characterized in that outlet pipes for removing the pulp-suspension subsequent to the measuring process are connected to the closed circuit via valves.

19. An arrangement according to claim 15, characterized in that the arrangement includes an open circuit for flushing clean the measuring cell including filter and inlet pipes and outlet pipes therefrom.

20. An arrangement according to claim 15, characterized in that the arrangement includes a pulp-suspension washing arrangement connected to the suspension-sample delivery pipe.

* * * * *